(12) United States Patent
Monteiro et al.

(10) Patent No.: US 7,976,841 B2
(45) Date of Patent: Jul. 12, 2011

(54) ANTI TFR ANTIBODY

(75) Inventors: Renato Monteiro, Montrouge (FR); Olivier Hermine, Palaiseau (FR); Ivan Moura, Paris (FR); Yves Lepelletier, Juvisy sur Orge (FR)

(73) Assignees: Institut National de la Sante et de la Recherche, Paris (FR); Centre National de la Recherche Scientifique, Paris (FR)

( * ) Notice: Subject to any disclaimer, the term of this patent is extended or adjusted under 35 U.S.C. 154(b) by 591 days.

(21) Appl. No.: 11/579,088

(22) PCT Filed: Apr. 30, 2004

(86) PCT No.: PCT/EP2004/005744
§ 371 (c)(1), (2), (4) Date: Jan. 23, 2008

(87) PCT Pub. No.: WO2005/111082
PCT Pub. Date: Nov. 24, 2005

(65) Prior Publication Data
US 2008/0193453 A1 Aug. 14, 2008

(51) Int. Cl.
*A61K 39/395* (2006.01)
*C07H 21/00* (2006.01)
*C07K 16/18* (2006.01)
(52) U.S. Cl. ............. 424/133.1; 530/387.1; 530/387.3; 536/23.4; 536/23.53
(58) Field of Classification Search .............. 424/133.1; 536/23.4, 23.53
See application file for complete search history.

(56) References Cited

U.S. PATENT DOCUMENTS
5,530,101 A * 6/1996 Queen et al. ............ 424/143.1
5,667,781 A 9/1997 Trowbridge et al.

OTHER PUBLICATIONS

Taetle et al. (Can. Res. 46: 1759-1763 (1986)).*
Trowbridge and Lopez (Proc. Natl Acad Sci USA, 79, 1175-1179, 1982).*
Taetle et al. (Cancer Res., 46, 1759-1763, 1986).*
White et al. (Cancer Res., 50, 6295-301, 1990).*
Lesley et al. (Mol Cell Biol. 5, 1814-21, 1985).*
MacCallum et al. (J. Mol. Biol. (1996) 262:732-745).*
De Pascalis et al. The Journal of Immunology (2002) 169, 3076-3084.*
Casset et al. (2003) BBRC 307, 198-205.*
Vajdos et al. (2002) J. Mol. Biol. 320, 415-428.*
Holm et al (2007) Mol. Immunol. 44: 1075-1084.*
Chen et al. J. Mol. Bio. (1999) 293, 865-881.*
Wu et al. J. Mol. Biol. (1999) 294, 151-162.*
Fujimori et al. (J. Nuc. Med. 31:1191-1198 (1990)).*
Beckman et al. (Can. 109:170-179 (2007)).*
Thurber et al. (Adv. Drug Deliv. Rev. 60:1421-1434 (2008)).*
Rudnick et al. (Can. Biotherp. & Radiopharm. 24: 155-162 (2009)).*
Moura, I.C., et al., "Identification of the Transferrin Receptor as a Novel Immunoglobulin (Ig)A1 Receptor and its Enhanced Expression on Mesangial Cells in IgA Nephropathy," Journal of Experimental Medicine, Tokyo, JP, Aug. 20, 2001, vol. 194, No. 4, pp. 417-425, XP002273386, ISSN: 0022-1007, cited in the application, the whole document.
Moura, Ivan C., et al., "A Neutralizing Monoclonal Antibody (mAb A24) Directed Against the Transferrin Receptor Induces Apoptosis of Tumor T Lymphocytes from ATL Patients," Blood, Mar. 1, 2004, vol. 103, No. 5, pp. 1838-1845, XP002313955, ISSN: 0006-4971, the whole document.
Written Opinion of the International Searching Authority ("ISA").

* cited by examiner

*Primary Examiner* — Lynn Bristol
(74) *Attorney, Agent, or Firm* — William E. Beaumont

(57) ABSTRACT

The invention relates to the monoclonal antibody A24 directed against the transferrin receptor. This antibody is in particular useful as an antiproliferative agent.

11 Claims, 12 Drawing Sheets

A

B

A

B

ANTI TFR ANTIBODY

CROSS-REFERENCE TO RELATED APPLICATIONS

The present application was filed under 35 USC 371, on Oct. 30, 2006, from PCT/EP2004/005744, filed on Apr. 30, 2004.

STATEMENT REGARDING FEDERALLY SPONSORED RESEARCH OR DEVELOPMENT

Not Applicable

THE NAMES OF PARTIES TO A JOINT RESEARCH AGREEMENT

Not Applicable

INCORPORATION-BY-REFERENCE OF MATERIAL SUBMITTED ON COMPACT DISK

Not Applicable

SEQUENCE LISTING

Not Applicable

BACKGROUND OF THE INVENTION

1. Field of the Invention

The invention relates to a new monoclonal antibody directed against the transferrin receptor (TfR), and to its use for the immunotherapy of hyperproliferative diseases, such as cancer.

2. Description of the Background

The transferrin receptor (CD71) is a disulfide-linked homodimeric transmembrane glycoprotein consisting of two 760-amino acid monomers of approximately 90 kDa each. TfR plays a crucial role in the regulation of iron uptake and cell growth (GILL et al., N Engl J. Med., 332, 1744-1748, 1995—HERMINE et al., N Engl J. Med., 332, 1749-1751, 1995). When diferric transferrin binds to its cell surface receptor, it is internalized via clathrin-coated pits to acidic vesicles where the iron-transferrin complex is dissociated. After release, the receptor and apo-transferrin recycle back to the cell surface.

TfR is constitutively expressed in cells of tissues that are constantly renewed, such as precursors of blood cells in the bone marrow, hepatocytes in the liver, keratinocytes in the epidermis and enterocytes in crypts of intestinal epithelium. Several studies have shown that TfR is expressed more abundantly in malignant tissues than in their healthy counterparts (GATTER et al., J Clin Pathol., 36, 539-545, 1983—FAULK et al, Lancet., 2, 390-392, 1980—SHINDELMAN et al, Int J Cancer, 27, 329-334, 1981).' Several authors have reported therapeutic approaches based on this idea using anti-TfR antibodies or transferrin itself conjugated to drugs to kill malignant cells.

It has also been proposed to use anti-TfR antibodies to block the interaction between transferrin and TfR, and consequently iron uptake, leading to iron deprivation and negative regulation of cell growth. However, although many publications describe the preparation of anti-TfR antibodies, there are very few reports of anti-TfR monoclonal antibodies (mAbs) having an antiproliferative activity.

TROWBRIDGE and LOPEZ (Proc. Natl Acad Sci USA, 79, 1175-1179, 1982) report the properties of a monoclonal antibody, designated 42/6 and typed as IgA (k), that blocks the binding of transferrin to its receptor and is able to inhibit in vitro the growth of an human T leukemic cell line, by blocking the cells in S phase of the cell cycle. The 42/6 antibody and the hybridoma producing it (ATCC HB-8094) are disclosed in U.S. Pat. No. 4,434,156.

TAETLE et al. (Cancer Res., 46, 1759-1763, 1986) have compared the 42/6 antibody with another anti-transferrin receptor monoclonal antibody (B3/25), which belongs to the IgG class, does not block the binding of transferrin to its receptor, and does not inhibit lymphocyte growth. They observed that transferrin did not inhibit 42/6 binding, suggesting that the inhibition of transferrin binding by antibody 42/6 inhibited results from a non-competitive, possibly steric, mechanism.

The 42/6 antibody has been tested in a Phase Ia trial, and it was observed that it was generally well tolerated, and that antibody concentrations that were capable of inhibiting malignant blood cell growth were obtained without toxicity. (BROOKS et al., Clin Cancer Res., 1, 1259-1265, 1995).

It was initially suggested that the antiproliferative properties of the 42/6 antibody were the result of its ability to block transferrin binding, thus depriving the cells of iron, and that other antibodies having the same ability would have the same antiproliferative properties. However, further studies have shown that the situation was more complicated.

WHITE et al. (Cancer Res., 50, 6295-301, 1990) and U.S. Pat. No. 5,667,781 disclose the effects of 42/6, B3/25, and 32 other monoclonal antibodies directed against the external domain of TfR (all of the IgG class), on the binding of transferrin to its receptor and on the growth of leukemic T-cells in tissue culture. No antibody other than 42/6 was found to be able to inhibit transferrin binding. Most of the IgG antibodies had no or little inhibitory effect on the growth of leukemic T-cells. Only one of them designated D65.30 and belonging to the IgG1 isotype, showed growth-inhibitory properties similar to those of 42/6, although it did not inhibit the binding of transferrin to TfR. Combinations of two or more of these anti-TfR monoclonal antibodies were also tested. Some of them did not differ in their growth-inhibitory effects from the individual antibodies, other were antagonistic, and some of them showed a synergistic growth-inhibitory effect. Some of these combinations showed a cytotoxic action, while the individual antibodies had a cytostatic action, or were inactive. These combinations of monoclonal antibodies with high antiproliferative properties did not block transferrin binding to TfR. Prolonged incubation, (48 h) of cells with the antiproliferative combinations B3/25 and 42/6, or D65.30 and A27.15, or with the individual antibodies B3/25, 42/6, or D65.30 induced a down-regulation of surface TfR expression resulting in a reduction of Tf binding at 4° C. and 37° C. However only 42/6 alone, and the combinations B3/25 and 42/6, or D65.30 and A27.15 were able to reduce TfR internalization.

LESLEY et al. (Mol Cell Biol. 5, 1814-21, 1985) have studied the effects of anti-murine transferrin receptor monoclonal antibodies belonging to either the IgG or the IgM class, on binding of transferrin and on murine lymphoma cell growth in vitro. They observed that the IgM inhibited cell growth but that the IgG did not, although they were able to induce a down-regulation and a degradation of the TfR. However, IgG cross-linked by an antiimmunoglobulin antibody were able to inhibit cell growth. In a subsequent work, the same team (LESLEY et al., Exp Cell Res., 182, 215-33, 1989) have studied the effects of IgG and IgM monoclonal anti-TfR antibodies and of their mono- and divalent fragments on murine lymphoma cell growth and TfR expression. They report that these effects depend on the degree of crosslinking of transferrin receptors by the antibody, which is a consequence of the antibody valence. Monovalent antibody fragments had no significant effects; divalent antibody fragments induced a down-regulation of cell-surface receptor expression without impairing its internalization and recycling and without impairing cell growth; multivalent IgM induced the accumulation of antibody-complexed receptor on the cell surface, blocking its internalization and resulting in a strong inhibition of cell growth.

It appears from the prior art cited above that the antiproliferative properties of anti-TfR antibodies strongly vary from an antibody to another and that they cannot be predicted on the basis of their ability to block or not transferrin binding to its receptor.

In a previous publication (MOURA et al., J Exp Med, 194, 417-425, 2001), the Inventors have reported that a monoclonal IgG (IgG2kappa), designated A24, produced by one of the hybridomas obtained from a mouse hyperimmunized with IgA-binding proteins, was in fact directed against the human TfR.

SUMMARY OF THE INVENTION

The Inventors have now found that the A24 antibody is able to block T cell proliferation, and that it appears to be more efficient than the previously described mAb 42/6 in inhibiting proliferation of T cells. They have studied the binding properties of A24 to TfR, and found that like 42/6, it inhibits the binding of transferrin to TfR; however, in contrast with 42/6, which inhibits transferrin binding to TfR by a non-competitive mechanism, A24 prevents Tf from binding to TfR in a competitive manner. A24 also reduced TfR expression and impaired TfR recycling.

The Inventors have also tested the effects of A24 on malignant T cells from acute and chronic forms of ATL (adult T-cell leukemia/lymphoma), that constitutively express high levels of surface TfR. They found that A24 was able to block the ex vivo proliferation of malignant T cells from both acute and chronic forms of ATL. In contrast with 42/6 which exerts its antiproliferative effects by blocking the cells at the S phase of the cell cycle, A24 acts by inducing the apoptosis of target cells.

BRIEF DESCRIPTION OF THE DRAWINGS

FIG. 5A,B illustrate the results of competition experiments which show that saturation of TfR with A24 partially impaired Fe-Tf binding and, reciprocally, saturation of TfR with Fe-Tf partially prevented A24 from binding.

DETAILED DESCRIPTION OF THE PREFERRED EMBODIMENTS

Figure 1:
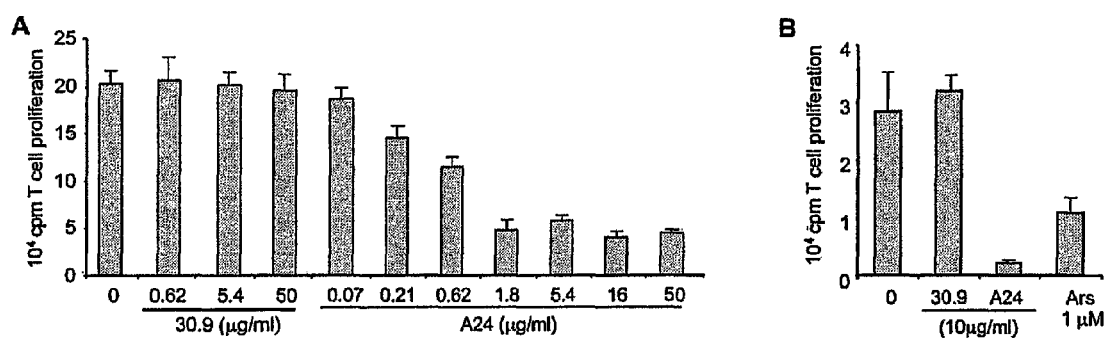
FIG. 1A illustrates the activity of A24 on peripheral blood leukocytes (PBMC) proliferation in efficiently reducing cell proliferation ($IC_{50}$ 0.5 µg/ml or 3 nM).
FIG. 1B illustrates strong inhibition of T cell proliferation (more than 90%) by A24. T cell proliferation was induced by co-culturing dendritic cells, activated by TNF-α and IL-1β, with resting T cells.

These observations have been recently published by the inventors (MOURA et al., Blood, 103, 5, 1838-45, 1 Mar. 2004; prepublished online Oct. 30, 2003).

However, these publications did not make the A24 antibody available.

The present invention provides the monoclonal antibody A24, which is useful in particular as a tool for therapeutic or research uses.

A24 belongs to the IgG2K subclass. The hybridoma A24 secreting this antibody has been deposited, according to the terms of the Budapest Treaty, with the CNCM (Collection nationale de Cultures de Microorganismes, 25 rue du Docteur Roux, Paris) on May 10, 2001, under number I-2665.

This hybridoma results from the fusion of the Ag8.653 mouse myeloma cell line with regional lymph node cells from a Balb/c mouse hyperimmunized with IgA-binding proteins derived from U937 cells.

A subject of the present invention is an antibody capable of binding specifically to the transferrin receptor and of blocking the binding of transferrin to said receptor, characterized in that it has the antigen-binding specificity of the antibody A24 produced by the hybridoma cell line CNCM I-2665.

The antigen-binding specificity of an antibody is determined by six complementarity determining regions (CDRs): three of them are provided by the light chain variable domain, and the three other are provided by the heavy chain variable domain. CDRI and CDR2 of light and heavy chains are encoded within the V gene segments. The most hypervariable CDRs, CDR3 of light and heavy chain, are generated by the recombination of V and J gene segments or V, D and J gene segments, respectively.

The antibodies of the invention include in particular:
the antibody A24 produced by the hybridoma CNCM I-2665;
the recombinant antibodies comprising at least CDR3, and preferably, the set of CDRI, CDR2, and CDR3, of the light and heavy chains of A24.

Said recombinant antibodies comprise in particular chimeric antibodies, where the constant region domains of the A24 antibody are replaced by human domains, and humanized antibodies, where the CDRs of A24 are inserted in framework regions (FRs) of human origin.

Methods for preparing recombinant antibodies are well known in the art. Polynucleotides encoding the variable regions of the anti-A24 antibody can easily be obtained by cloning said variable regions from a cDNA library of the hybridoma A24. These polynucleotides can be associated with polynucleotides encoding the constant region domains of an human antibody, to obtain a chimeric antibody. Alternatively, to obtain an humanized antibody, the nucleotidic sequences encoding the CDRs of A24 can be identified within the variable region, and incorporated into the framework regions of a human antibody, using techniques of CDR grafting, which is generally completed by framework optimization, consisting in the replacement of some residues of the human framework, in order to retain maximum binding affinity. Methods for humanizing antibodies are known in themselves and are described for instance by ROUTLEDGE et al. ["Reshaping antibodies for therapy", in Protein Engineering of Antibody Molecules for Prophylactic and Therapeutic Applications in Man, 13-44, Academic Titles, Nottingham, England (1993)] or by ROGUSKA et al. Protein Engineering, 9(10), 895-904, (1996)]. The step of framework optimization has been recently simplified by the use of combinatorial libraries (ROSOK. et al. J. Biol. Chem. 271, 22611-22618, 1996; BACA et al. J. Biol. Chem. 272, 10678-10684, 1997). Another recent strategy for antibody humanization preserves only the original nonhuman CDR3 sequences of light and heavy chain while the remaining sequence is selected from naïve human V gene libraries (RADER et al., Proc. Natl. Acad. Sci U.S.A. 95, 8910-8915, 1998).

The present invention also includes:
the Fv, Fab, or Fab'2 fragments of the antibody A24, or of the chimeric or humanized antibodies obtained from A24;
the recombinant proteins comprising an antibody of the invention or a Fv, Fab, Fab'2 or scFv fragment thereof fused to an heterologous polypeptide. Said recombinant proteins may be for instance:
scFv fragments consisting of the variable portions of the heavy and light chains of an antibody, connected to one another via a flexible peptidic linker [CLACKSON et al., Nature, 352, 624-628, (1991)], thus forming a single-chain protein
divalent or plurivalent derivatives of scFv fragments, such as "diabodies" or "triabodies", resulting from the association of 2 or 3 scFv fragments;
proteins combining at least one antibody fragment comprising the CDRs of the antibody A24, with a molecule having pharmacological activity (for example a toxin) or effector properties (for example an Fc fragment).

Another object of the present invention is a polynucleotide encoding the light chain or the heavy chain of an antibody of the invention, or a Fv, Fab, Fab'2 of the invention, or a recombinant protein of the invention.

According to a preferred embodiment, said polynucleotide is selected among:
a polynucleotide encoding a protein comprising the CDRs of the light chain of the antibody A24;
a polynucleotide encoding a protein comprising the CDRs of the heavy chain of the antibody A24.

The invention also includes also any recombinant vector, in particular any expression vector, comprising a polynucleotide of the invention.

A subject of the present invention is also any cell expressing an antibody, or a Fv, Fab, or Fab 2 fragment, or a recombinant protein of the invention. This encompasses in particular the hybridoma CNCM I-2665, and also the host cells transformed with a polynucleotide of the invention.

The invention also includes the monoclonal antibodies recognizing the same epitope as A24. This epitope can be identified by screening with A24 a library of fragments from the TfR1 ectodomain, for instance library of overlapping peptides of defined length covering the whole sequence of said ectodomain, or by screening with A24 a collection of mutants of the TfR1 ectodomain, such as those described by (WEST et al., J Mol Biol. 2001, 313(2):385-97), to identify the residues involved in the conformation of the epitope.

Once a peptide binding to A24 has been identified, it can be used for immunizing animals in order to prepare monoclonal antibodies directed against said peptide, and/or for screening hybridomas producing anti-TfR antibodies, or for screening combinatorial libraries of genes derived from human antibody genes.

The antibodies, antibody fragments, or recombinant proteins of the invention, can be used in particular to obtain medicinal products.

The finding by the inventors that A24 can not only inhibit cell proliferation, but also induce apoptosis of highly proliferating T cells, without inducing apoptosis of non proliferating normal PBMC, allows to propose the antibodies of the invention as a new treatment for the immunotherapy of tumors, in particular tumors expressing a high level of TfR.

This includes hematologic tumors, such as lymphomas, in particular ATL, MCL, Hodgkin Disease, Large B cell lymphoma, Peripheral T cell lymphoma, Acute leukaemia (Myeloid and Lymphoid) as well as solid tumors, such as Renal carcinoma, Lung cancer (small cells), etc.

The antibodies of the invention can also be used in the treatment of HTLV-1 related diseases, to reduce the viral load in inflammatory disorders associated with HTLV-1 infection, including HAM/TSP, polymyositis, and arthritis.

The invention also encompasses a therapeutic composition comprising an antibody of the invention or a fragment thereof, and a pharmaceutically acceptable carrier.

Although the antibodies of the invention are efficient by themselves in killing tumor cells, they can be associated with one or more other therapeutic agent(s).

In particular, they can be associated with one or more antiviral and/or antitumor agent(s), such as AZT, IFN-α, anti-CD20 mAb, anti-CD25 mAb, chemotherapy agents such as adriablastin, aracytine, vincristin, etc). Further, due to their greater affinity for tumor cells expressing a high density of TfR than for normal cells, the antibodies of the invention can be used to target antitumor agents to said tumor cells. Thus, according to a preferred embodiment of a composition of the invention, said other therapeutic agent(s) is (are) conjugated to an antibody of the invention. Advantageously, said other therapeutic agent(s) is (are) contained in liposomes that are coupled to an antibody of the invention.

The inventors have also found that A24 blocks IgA-mediated proliferation of mesangial cells. This finding allows to propose the antibodies of the invention as a new treatment for the immunotherapy of IgA nephropathy, in particular IgA nephropathy with high mesangial proliferative status.

The present invention will be understood more clearly from the further description which follows, which refers to non-limitative examples illustrating the properties of the A24 antibody

MATERIALS AND METHODS

Reagents and Antibodies

IL-2 and PHA were both from Roche Diagnostics, France. Anti-CD25-FITC, Anti-CD3 APC, anti-TfR-PE, irrelevant mouse IgG-FITC, mouse IgG-APC and mouse IgG-PE isotype controls were all from rmmunotech, France. Chemotherapeutical agents were used at the following concentrations: Zidovudine (AZT) (Wellcome Research Labs, Beckenham, Kent, UK) at 0.2 µM, anti-IL-2Rα monoclonal antibody (Zenapax from Hoffmann-La Roche, Nutley, N.J.) at 10 µg/ml, IFN-α (Hoffman-La Roche, Basel, Switzerland) at 100 U/ml and arsenic trioxide (Sigma Chemical Co.) at 1 µM. The anti-human TfR (CD71) monoclonal antibody A24 was obtained from a culture of the hybridoma CNCM I-2665 and the isotype-matched monoclonal antibody 30.9 directed against the rat FcεRI-chain was used as a control (PASTORELLI et al., Mol Immunol., 38, 1235, 2002). Protein concentrations were determined by the BCA method as recommended by the manufacturer (Pierce).

Isolation and Culture of Cells.

Peripheral blood mononuclear cells (PBMC) were isolated as described earlier by the standard Ficoll-Paque method (Amersham Life Science, Buckinghamshire, U.K.) (BAZARBACHI et al, Blood., 93, 278-283, 1999). The healthy volunteers and the 4 acute and 3 chronic ATL patients (classified following Shirono criteria) (SHIRONO et al., Leukemia., 8, 1834-1837, 1994) had all given their informed consent. ATL tumor cells represented between 60-90% of the T cell population. Each cell type was freshly cultured in conditioned RPMI-1640 medium supplemented with 10% of fetal calf serum (FCS, Gibco BRL) and a mixture of interleukin-2 (20 U/ml IL-2) and phytohemagglutinin (4 µg/ml PHA). Mixed leukocyte reaction (MLR) was performed as described earlier (TORDJMAN et al., Nat Immunol., 3, 477-482, 2002). CIB tropical spastic paraparesis (HAM/TSP) cell line was cultured in RPMI-1640 medium supplemented with 10% of FCS.

Flow Cytometry.

For single, double, and three-color flow cytometry, cells were incubated for 15 minutes at 4° C. in phosphate-buffered saline (PBS), 2% FCS, and 0.1% $NaN_3$, with FITC-, APC- and PE-conjugated anti-CD25, anti-CD3 and anti-CD71 specific antibodies or with control isotype-matched irrelevant antibodies at the appropriate concentration (Imnunotech, Beckman Coulter). After washing, $2 \times 10^4$ events were analyzed with a FACScan (Becton Dickinson).

Confocal Microscopy.

CIB cells were plated on poly-L-lysine (Sigma, St Louis, Mo.) coated slides and incubated for 30 minutes at 4° C. Cells were then labeled with the monoclonal antibody A24 at 10 µg/ml during 30 minutes at 4° C. After two washes in PBS/2% FCS, cells were plated in RPMI-1640 10% FCS for various times at 37° C. or kept on ice. Cells were then fixed in 1% paraformaldehyde, quenched with 0.1 M glycine, and permeabilized with 1% saponine in PBS containing 1% bovine serum albumin. Primary antibodies were revealed by a goat anti-mouse IgG conjugated to Cy-5 (Jackson ImmunoResearch, USA). After two additional washes in PBS/2% FCS, cells were incubated for 5 min with 2 µg/ml wheat-germ agglutinin (WGA) conjugated to Alexa-488 to delineate the plasma membrane and washed again. Mounted slides were examined with a confocal laser microscope system (LSM 510 Carl Zeiss, Germany).

Proliferation Assay.

PBMC were resuspended in RPMI-1640 with 10% FCS, and added in triplicates at the concentration of $10^5$ cells/well in 96-well tissue culture plates (Falcon, Oxnard, Calif.). Proliferation was measured over 18 h, using pulses with 1 µCi/well of [$^3$H]-thymidine (Amersham Life Science, Buckinghamshire, U.K.). Cells were then harvested with a 96-well Harvester (Pharmacia, St. Quentin, France), collected on filters (Pharmacia) and the incorporation of [$^3$H] thymidine was measured with β-plate microscintillation counter (LKB, Pharmacia).

Assay for Apoptosis.

Two million of PBMC from HTLV-1 patients were treated for 96 h with IL-2 and PHA in the presence or absence of A24 (10 µg/ml), 30.9 (10 µg/ml) or of the apoptosis-inducing agent VP16 (100 ng/ml). Cells were then washed with ice-cold PBS and incubated with a combination of annexin V-FITC and propidium iodide (PI) (Beckman-Coulter, Marseilles, France), according to the manufacturer recommendations. Alternatively, the apoptosis was evaluated through mitochondrial membrane depolarization with the DIOC staining (Molecular Probes) as described earlier (ZERMATI et al., J Exp Med., 193, 247-254, 2001).

[$^{55}$Fe] Transferrin Uptake Studies.

Apo-transferrin was loaded with [$^{55}$Fe] to 99% saturation as described (KOTAMRAJU et al., J Biol Chem., 277, 17179-17187, 2002). PBMC cultured at $1 \times 10^6$/ml for 48 h in PHA/IL-2 conditioned medium were exposed to 2.5 µM of [$^{55}$Fe]-transferrin for the times indicated. At the end of the uptake time, cells were washed 4 times in PBS and lysed in 0.1% Triton X-100 in PBS. Radioactivity per g of protein in the lysates was counted in a beta-counter.

Surface Plasmon Resonance Assays.

All the assays were performed on a Biacore 2000 instrument equilibrated at 25° C. with PBS+0.005% Tween-20 at a flow rate of 50 μl/min. The Penta-His monoclonal antibody (Qiagen) was covalently immobilized on the carboxymethylated surface of a CM5 sensorchip, using the Amine Coupling Kit (Biacore AB). Production and purification of soluble TfR was previously described (LEBRON et al., Cell., 93, 111-123, 1998). Recombinant (His)$_6$-tagged TfR1 ectodomain (TfR-(His)$_6$) was captured to a level of 120 resonance units (low density) or 1650 resonance units (high density) on the anti-(His)$_6$ surface. Ten different concentrations of mAb A24 (1-500 nM) or of Fe-transferrin (0.25-150 nM) were then injected across the anti-(His)$_6$MR-(His)$_6$ surface for 4 minutes, and the dissociation of the complexes was followed for 5 minutes. Control experiments were performed by injecting A24 or Fe-transferrin directly onto the anti-(His)$_6$ surface. The association and dissociation profiles were analyzed with a non-linear least squares algorithm implemented in the Biaevaluation 3.0 software (Biacore AB), using single-exponential functions of time. For the competition experiments, saturating A24 or Fe-transferrin (300 nM) were injected onto the low density anti-(His)$_6$/TfR-(His)$_6$ surface, followed one minute later by respectively Fe-transferrin or A24 (15 nM). The resulting association profiles were compared with those obtained without the preliminary saturation step (control injection of buffer).

Example 1

Activity of A24 on PBMC Proliferation

To investigate the activity of A24 on peripheral blood leukocytes (PBMC) proliferation, cells were activated with PHA/IL-2 and incubated with different concentrations of A24 (0 to 50 μg/ml) or control antibody (30.9) (0 to 50 μg/ml) for 72 h before [$^3$H]-thymidine incorporation. The results are shown in FIG. 1A. A24 efficiently reduced cell proliferation (IC$_{50}$ 0.5 μg/ml or 3 nM). By contrast, 30.9 did not interfere with PHA/IL-2-induced cell proliferation.

To test if A24 could also block physiologically activated T cell proliferation, we examined the effect of A24 in allogeneic Mixed Leukocyte Reaction (MLR). DC-induced allogenic T cell proliferation was evaluated after 6 days of culture in the presence of A24, control antibody (30.9) or arsenic trioxide (Ars). The results are shown in FIG. 1 B. Data represents means SD of one out of three separate experiments.

Co-culture of dendritic cells, activated by TNF-α and IL-1β, with resting T cells induced T cell proliferation. Upon addition of A24 to the co-cultured cells, a strong inhibition of T cell proliferation was observed (more than 90%). Arsenic trioxide (Ars) a compound that was previously shown to induce apoptosis of activated T cells (BAZARBACHI et al, Blood., 93, 278-283, 1999) was also shown to block T cell proliferation.

Example 2

TfR Expression and Antiproliferative Effect of A24 on Tumor Cells

The differential expression of TfR in freshly isolated and in in vitro cultures of T cells from healthy individuals and from patients suffering from acute and chronic forms of ATL was studied.

Figure 2:
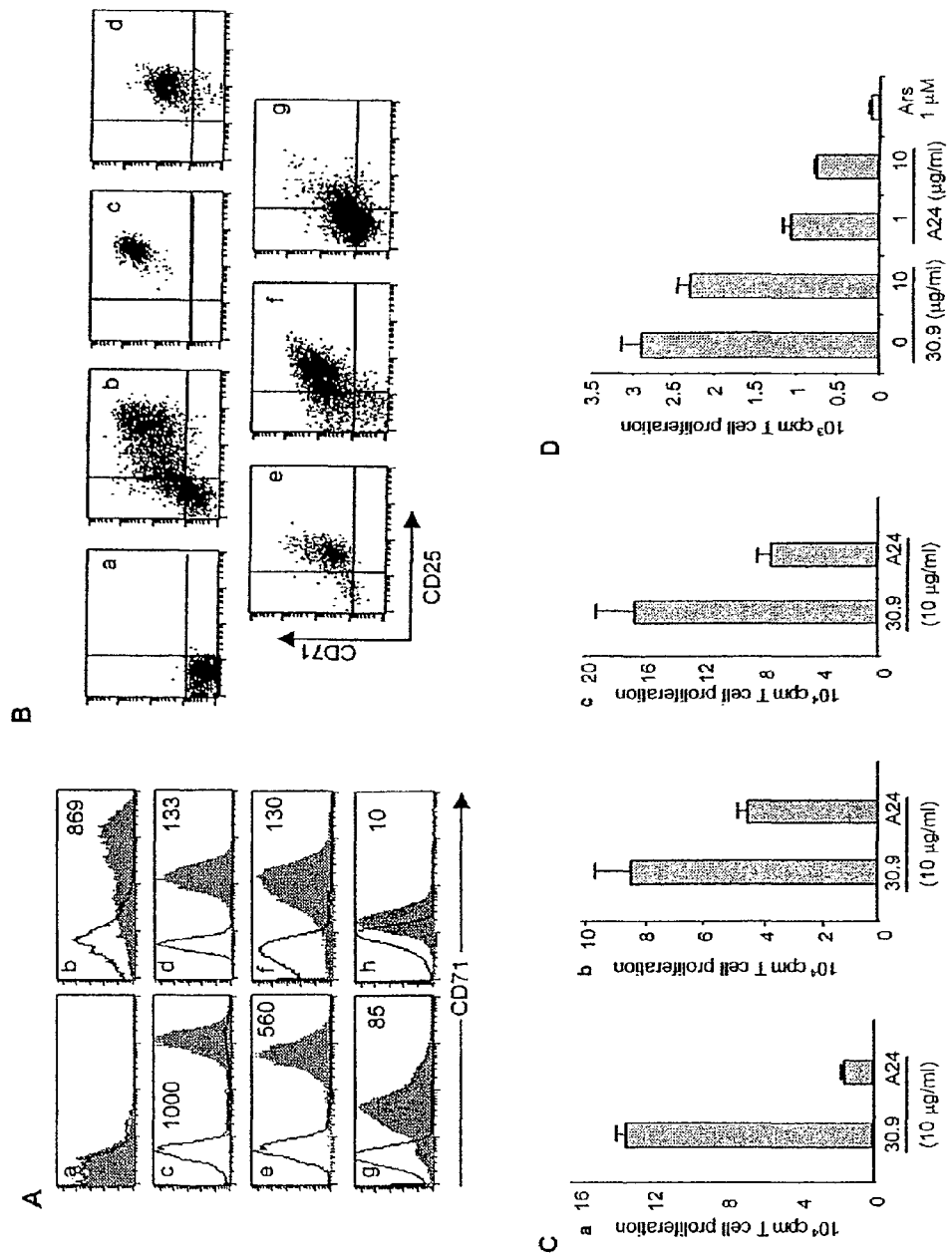
FIG. 2A illustrates differential expression of TfR in freshly isolated and in in vitro cultures of T cells from healthy individuals and from patients suffering from acute and chronic forms of ATL.
FIG. 2B illustrates co-expression of TfR and CD25 in healthy and tumor cells. T cells from chronic forms of ATL expressed both CD25 and TfR at a lower level than T cells from acute forms of ATL.
FIG. 2C illustrates that A24 significantly blocked cell proliferation in cultures of cells from both acute and chronic forms of ATL.
FIG. 2D illustrates that a single dose of A24 added during the first day of Culture significantly inhibited the proliferation of infected (with HTLV-1) T cell clones.
Figure 3:
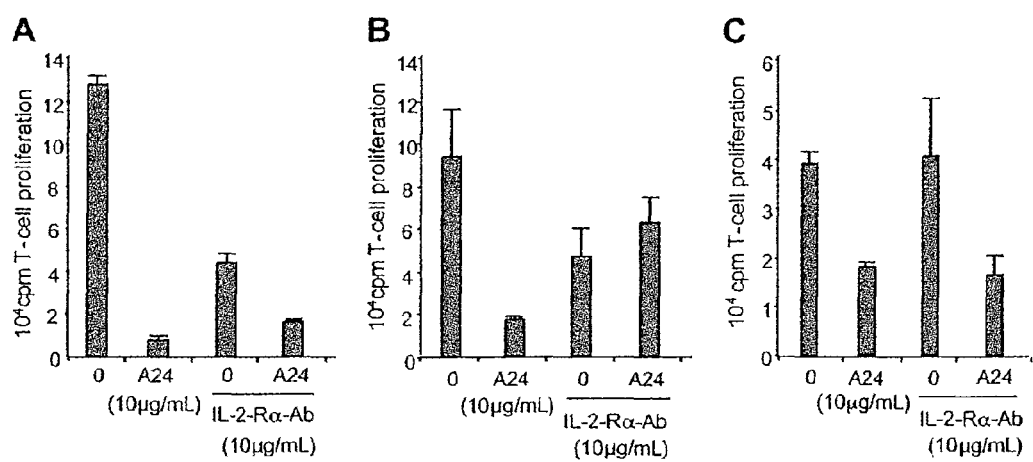
FIGS. 3A, B and C illustrate a comparison of the abilities of A24 and anti-IL-2Rα to block ex vivo proliferation of HTLV-1 infected cells. Peripheral blood leukocytes from healthy individuals (A), and chronic (B) and acute (C) forms of ATL were incubated with PHA and IL-2 for 72 h with A24, anti-IL-2Rα or both. Anti-IL-2Rα significantly inhibited the proliferation of cells from both normal individuals and patients with chronic forms of ATL, it did not block the proliferation Of cells derived from acute ATL patients; whereas A24 significantly inhibited the proliferation of cells from patients suffering from either acute or chronic forms of ATL.

The results are shown on FIG. 2A. TfR expression was examined on different cell subtypes: resting T cells (a), PHA/IL-2 activated T cells (b), lymphoma cell line (Jurkat) (c), HTLV-1 positive cell lines (HUT-102 and MT-2 respectively) (d, e), ex vivo lymphocytes of acute ATL patients (f, g), ex vivo lymphocytes of patients with a chronic ATL form (h). The expression level of TfR was expressed on histograms plotting the fluorescence intensity of anti-CD71 (gray) as compared to that of the isotype control (open line). As reported earlier (NECKERS, Pathobiology., 59:11-18, 1991), non-infected and non-stimulated T cells (gated as CD3-positive cells) showed a weak expression of TfR, whereas PHA/IL-2 activated T cells expressed high levels of TfR. HTLV-1-infected T cells from acute forms of ATL expressed TfR at levels higher than those observed in T cells from chronic ATL forms. HUT-102 and MT2 cell lines (HTLV-1 transformed cell lines) expressed TfR at lower levels than in the Jurkat T cell line.

CD25 expression was tested to verify whether TfR expression was correlated to the extent of T cell activation. The co-expression of TfR and CD25 on healthy and tumor cells is shown on FIG. 2B: Legend of FIG. 2B: Resting T cells (a), PHA/IL-2 activated T cells (b), HTLV-1 positive cells line (MT-2 and HUT-102 respectively) (c, d), ex vivo lymphocytes of patients with an ATL acute form (e, f), ex vivo lymphocytes of patients with an ATL chronic form (g).

T cells from chronic forms of ATL expressed both CD25 and TfR at lower level than T cells from acute forms of ATL. Cultures of leukemic T cells derived from ATL patients in the presence of PHA/IL-2 retained their activated phenotype (data not shown).

We then looked into the possibility of using A24 as an inhibitor of proliferation in cultures of PBMC derived from ATL patients.

PBMC from healthy individuals (a) and HTLV-I infected patients with an acute ATL (b) or a chronic ATL (c) were plated in culture wells with A24 or a control antibody (30.9) in the presence of PHA/IL-2, for 72 h before [3H] thymidine incorporation. The results are shown on FIG. 2C.

Although somewhat less efficiently than in PBMC from healthy individuals, A24 significantly blocked cell proliferation in cultures of cells from both acute and chronic forms of ATL.

HTLV-1 infected cells can proliferate in vitro, but the clones that proliferate in culture are generally not the same as those that proliferate in the patient. To verify if A24 could inhibit the emergence of HTLV-1 infected T cell clones, we cultured cells freshly isolated from patients and from healthy individuals in the presence or absence of A24. PBMC from HTLV-1 infected patients with a chronic ATL form were plated in culture wells with the 30.9, A24 or Ars for 2 weeks. Emergence of HTLV-1 clones was evaluated by [3H] thymidine incorporation. After 2 weeks of culture, the appearance of proliferating cells was assessed by [3H] thymidine incorporation.

The results are shown on FIG. 2D. Data are means SD of one out of at least three separate experiments with 4 acute and 3 chronic ATL patients.

A single dose of A24 added during the first day of culture significantly inhibited the proliferation of infected T cell clones. Control antibody 30.9 had no statistically significant effect on HTLV-I clone proliferation. As a positive control, Ars was more efficient than A24 in blocking tumor T cell proliferation.

Example 3

Comparative Activities of A24 and Anti-IL-2a on Cell Proliferation in Acute and Chronic Forms of ATL TfR expression is essential for the proliferation of both normal and malignant T cells. While TfR expression in normal T cells is tightly coupled to interleukin-2 receptor expression, TfR expression in malignant cells is usually constitutive. It was previously shown that the anti-IL-2Rα can efficiently block the ex vivo proliferation of cells derived from chronic ATL patients. However, anti-IL-2Rα was less or not efficient in blocking the proliferation of cells from acute forms of ATL (WALDMANN et al, Blood, 82, 1701-1712, 1993, WALDMANN, J Clin Immunol., 22, 51-56, 2002). Thus, we compared the abilities of A24 and anti-IL-2Rα to block the ex vivo proliferation of HTLV-1 infected cells. Peripheral blood leukocytes from healthy individuals (a), and chronic (b) or acute (c) forms of ATL were incubated with PHA and IL-2 for 72 h with A24, anti-IL-2Rα or both. Proliferation of these cells was then measured by [$^3$H] thymidine incorporation. Data are means SD of one out of at least three separate experiments with 4 acute and 3 chronic ATL patients.

While anti-IL-2Rα significantly inhibited the proliferation of cells from both normal individuals and patients with chronic forms of ATL, it did not block the proliferation of cells derived from acute ATL patients, hi contrast, A24 significantly inhibited the proliferation of cells from patients suffering from either acute or chronic forms of ATL. Association of A24 and anti-IL-2Rα in healthy individuals and acute ATL forms have no synergistic effect whereas in chronic ATL forms the effect of combined immunotherapy in cell proliferation was less efficient than A24 treatment alone.

Example 4

Comparative Activities of A24, AZT, IFN-α, VP16 and Arsenic Trioxide on the Proliferation of Tumor Cells We next examined the effect of the association of A24 with different chemotherapeutic agents on malignant ATL cell proliferation.

Tumor cells from a chronic ATL patient were incubated with or without A24, and treated with or without different chemotherapeutic agents such as AZT, IFN-α or both AZT and IFN-α, Ars or VP16 for 72 h to determine the potential synergistic effect of these agents with A24. Cells were pulsed with [$^3$H] thymidine and harvested, before measuring the incorporation of [$^3$H] thymidine. Data are means SD of one representative experiment of three separate experiments.

Figure 4:
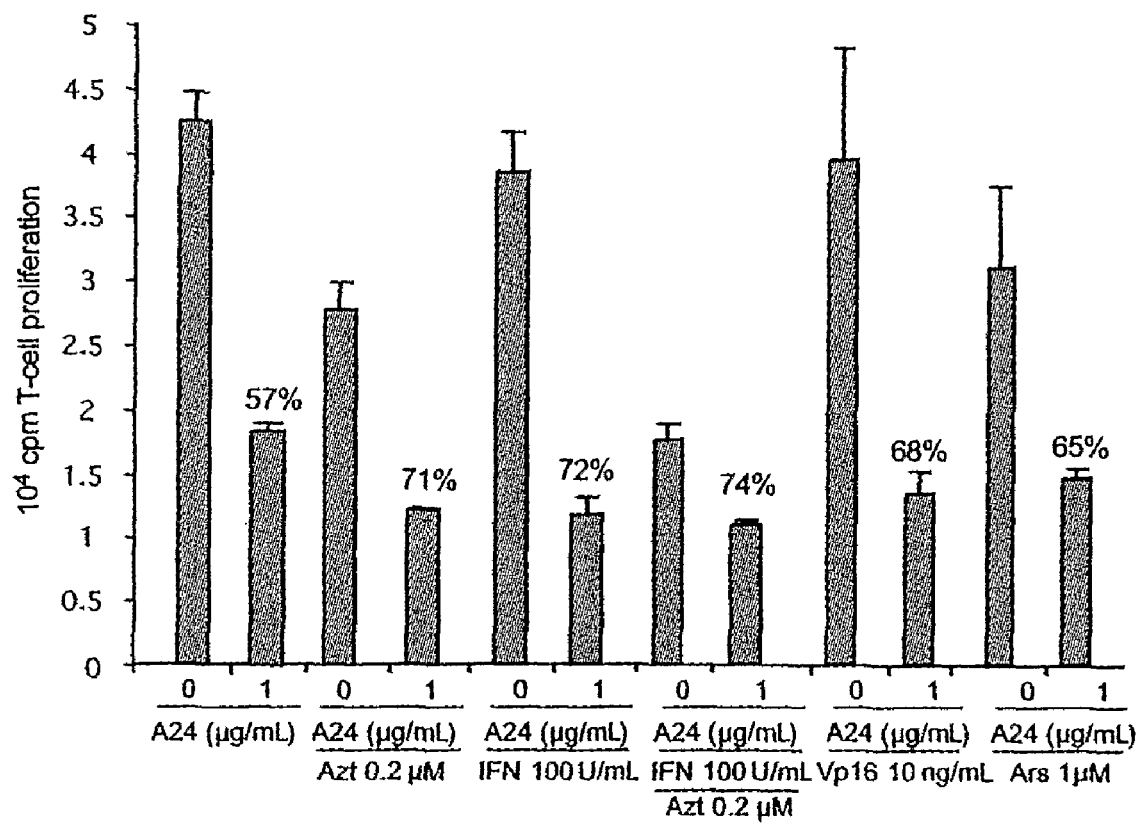
FIG. 4 illustrates that association of chemotherapeutic agents, such as AZT or IFN-α, with A24 can improve the inhibition of tumor cell proliferation. Approximately 70% inhibition was observed when A24 is associated with AZT, IFN-α or both together.

The results shown on FIG. 4. The association of chemotherapeutic agents with A24 can improve the inhibition of tumor cells proliferation. The major inhibitory effect is observed when A24 is associated with AZT, IFN-α and AZT+IFN-α (approximately 70% inhibition of cell proliferation).

Example 5

Binding Properties of A24 to TfRI

A24 Competes with Fe-Tf for TfR Binding

To gain insight into the mechanism of inhibition of cell proliferation by A24, a series of surface plasmon resonance experiments were performed to determine the binding properties of mAb A24 and Fe-Tf to the soluble TfRI ectodomain. The determination of $k_{on}$, $k_{off}$ and K'd from Biacore experimental data is described in Materials and Methods. The results are shown in Table I below. The mean value and associated standard error of three or more independent determinations is given.

TABLE I

| Density of immobilized receptor | Ligand | $k_{on}$ ($10^5$ M$^{-1}\cdot$s$^{-1}$) | $K_{off}$ ($10^{-4}$ s$^{-1}$) | K'd$^b$ (nM) |
|---|---|---|---|---|
| Low | Fe-Tf | 12.1 ± 1.70 | 11.9 ± 1.9 | 0.98 ± 0.21 |
| Low | mAb A24 | 8.30 ± 0.64 | 22.3 ± 4.8 | 2.69 ± 0.62 |
| High | Fe-Tf | 3.04 ± 0.63 | 9.48 ± 2.24 | 3.12 ± 0.93 |
| High | mAb A24 | 3.82 ± 0.12 | 3.88 ± 0.91 | 1.02 ± 0.24 |

$^b$K'd is the equilibrium dissociation constant measured at the heterogeneous interface between the liquid phase and the sensorchip surface. There is no simple relation between this constant and the Kd that would be measured in a homogeneous solution-A24 interacted with TfR with an equilibrium constant (K'$_d$) of 2.69 nM, compared to 0.98 nM for Fe-Tf.

Figure 5:
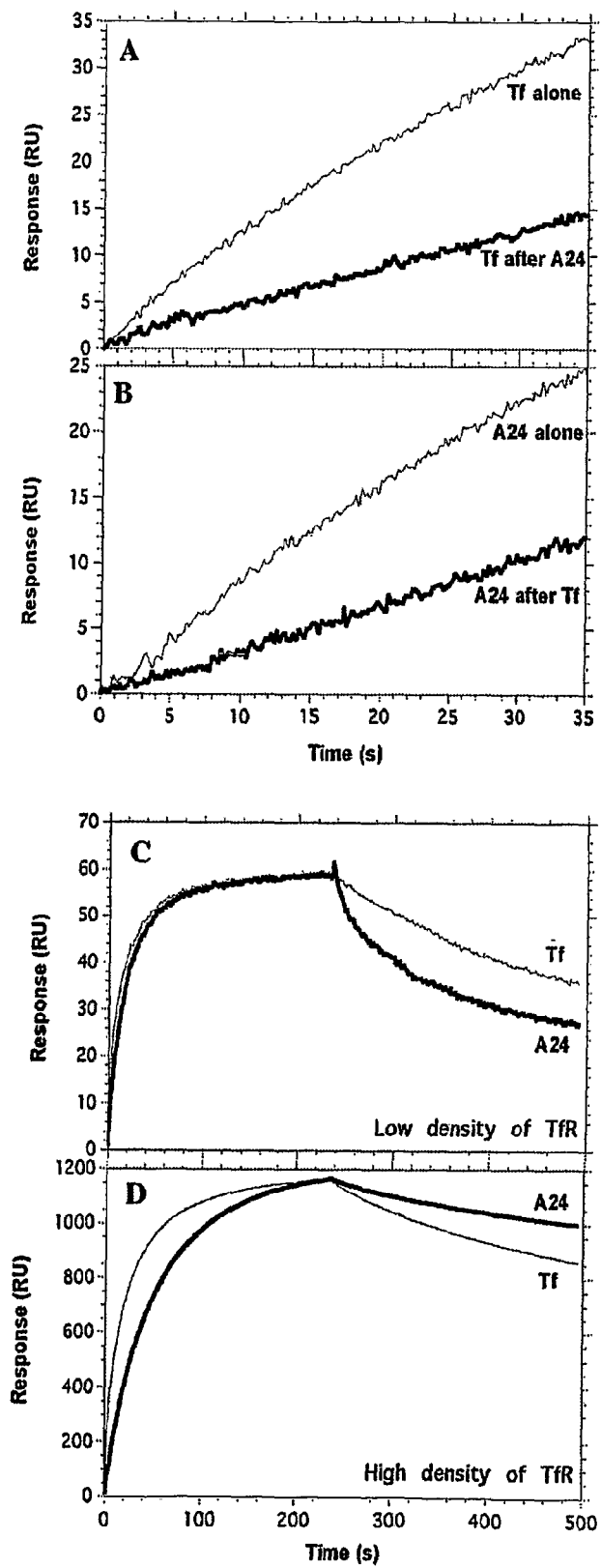
FIG. 5 C,D illustrate the results of injecting a series of concentrations (low density (C) and high density (D)) of Fe-Tf and A24 across an immobilized TfR surface, which indicate that A24 preferentially binds to cells expressing high levels of TfR, i.e., malignant cells.

We then performed competition experiments to determine if the A24 binding sites on TfR overlapped with those of Fe-Tf. Experimental conditions are described in the Material and Methods section above. (FIGS. 5 A and B)

5A) Tf was injected across the TfR surface, after saturation with A24 (bold line) or a control buffer injection (thin line).

5B) A24 was injected across the TfR surface, after saturation with Tf (bold line) or a control buffer injection (thin line).

The saturation of TfR with A24 partially impaired Fe-Tf binding and, reciprocally, the saturation of TfR with Fe-Tf partially prevented A24 from binding.

The apparent stability of the complex between A24 and TfR is strongly dependent on the density of TfR.

The affinity of A24 for a low density surface of TfR was 3 times lower than that of Fe-Tf. However, unlike the monovalent ligand Tf, A24 possesses two binding sites, and therefore the avidity of this bivalent IgG could be dependent on the available density of the receptor on the cell surface. To mimic this situation, we captured different amounts of TfR-(His)$_6$ on a anti-(His)$_6$ sensorchip.

A series of concentrations of Fe-Tf and A24 was injected across a low density (C: 120 RU) or a high density (D: 1650 RU) immobilized TfR surface: only the data obtained for 134 nM of Fe-Tf (thin line) and 62.5 nM of A24 (bold line) are shown. A24/TfR complexes dissociate faster than Tf/TfR when TfR is present at low density (C), while at high density, the opposite situation is observed (D) (see Table I).

The dissociation rate (off) of the A24/TfR complex was 6 times lower when TfR was available at higher densities, hi contrast, the off, and therefore the t1/2, of the Fe-Tf/TfR complex was not influenced by the density of TfR (Table I and FIGS. 5 C and D). This experiment suggests that A24 will preferentially bind to cells expressing high levels of TfR, i.e. malignant cells.

Example 6

Effect of A24 on the Uptake of Transferrin and the Recycling of TfR

A24 Inhibits the [$^{55}$Fe] Tf Uptake by Activated T Cells

The results presented above suggested that by interfering with Fe-Tf association with TfR, A24 could inhibit Fe-Tf uptake.

To test this hypothesis, PBMC from normal donors were cultured in PHA/IL-2 conditioned medium and were incubated with [$^{55}$Fe]-Tf in the presence of A24 (at 10 μg/ml) or of an irrelevant isotype-matched control (antibody 30.9).

PBMC were incubated with PHA and IL-2 for 24 h before being plated in culture. To assay Tf uptake, activated cells were incubated for different time intervals with A24 (open bar) or 30.9 isotype control (gray bar) in the presence of 2-5 μM ($^{55}$Fe)-Tf. Data are means SD of one experiment out of three separate experiments.

Figure 6:
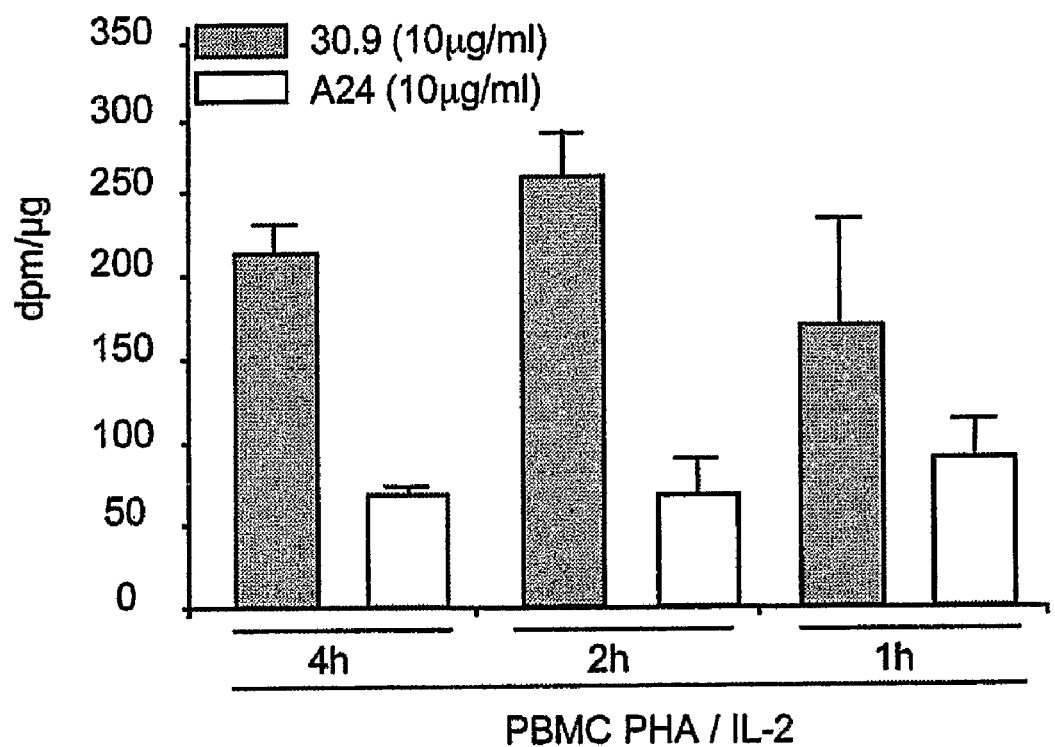
FIG. 6 illustrates that A24 drastically inhibited $^{55}$Fe-Tf uptake in PHA/IL-2 activated T-cells, reaching a maximum of 80% inhibition after 2 hours of culture.

As shown in FIG. 6A, A24 drastically inhibited [$^{55}$Fe]-Tf uptake in PHA/IL-2 activated T cells, reaching a maximum of 80% inhibition after 2 hours of culture.

A24 Impairs TfR Expression and Recycling.

Endocytosis of transferrin via TfR is a well-established phenomenon. Diferric transferrin binds to TfR on the cell surface and is endocytosed in peripheral cytoplasmic sorting endosomes (pH 6.2) and recycling endosomes (pH 6.4). After Fe dissociation, apo-transferrin and TfR recycle back to the cell surface. It was previously shown that cross-linking of TfR by anti-TfR antibodies could induce the down-regulation of TfR expression in tumor cells.

To examine whether A24 could affect TfR expression at the cell surface, we cultured non-stimulated or stimulated PBMC in the presence or absence of A24. Expression of TfR and CD25 was followed on PBMC from healthy donor (a), chronic (b) and acute (c) ATL patients. Cells were activated with PHA and IL-2 for 72 h, in the presence of A24 or a control antibody (30.9). The results are shown on FIG. 6B.

The inhibition percentage of the mean fluorescence intensity linked to TfR and CD25 expression is indicated in histograms located at the up-right corner of right panels.

A24 drastically down-regulated TfR at the cell surface in normal cells stimulated by PHA/IL-2 (FIG. 6B). In addition, A24 down-regulated the expression of TfR in ex vivo cell cultures from chronic and acute forms of ATL by more than 75%, and it did not interfere with CD25 expression (FIG. 6B). A24 had no effect on the expression of TfR in normal non-activated T cells (data not shown). As ATL cells produce high levels of both IL-2 and IL-15, we also tested the effect of A24 on HTLV-1 infected cells from acute ATL donors cultured in IL-15 or IL-2/IL-15 conditioned medium. We observed a more than 65% down-regulation of TfR expression in both cases (data not shown).

TfR is constantly recycled in the cell with a $t_{1/2}$ as low as 15 minutes. To test the ability of A24 to interfere with this recycling, malignant activated T cells (CIB cell line, derived from a HTLV-1 patient) were stained at 4° C. with A24 and plated under culture conditions at 37° C. for different times (0 to 180 min) to determine the effect of A24 binding on TfR trafficking. After 30 minutes of incubation at 4° C., cells were washed, cultured at 37° C. for up to 180 min, and A24 was localized by confocal microscopy. Cells that were only incubated at 4° C. expressed the TfR complex in their membrane, as evidenced by the co-localization of A24 and WGA. After 15 minutes of culture, the presence of TfR in sub-membrane vesicular compartments was consistent with TfR recycling. However, after longer periods of culture, these A24-decorated TfR had not recycled to the cell surface, but instead, they had been directed to polarized intracellular compartments resembling endo-lysosomal vesicles. (FIG. 6C).

Example 7

A24 Induces Apoptosis of Activated ATL Tumor Cells

Fe deprivation induces a variety of consequences, such as the reduction of cell proliferation and the activation of programmed cell death (HAQ et al., Exp Hematol., 23, 428-432, 1995), a phenomenon associated with phosphatidylserine exposure and mitochondrial membrane depolarization. To determine whether A24 induced apoptosis, cells treated with A24 were assayed for the translocation of phosphatidylserine from the inner to the outer leaflet of the plasma membrane by using the annexin V affinity assay. The results are shown of FIGS. 7A and 7B.

Comparative effect of A24, 30.9 and VP 16 on the induction of programmed cell death in selected cells. Cells were activated or not with PHA and IL-2 and incubated in the presence of 30.9, A24 and VP16. Apoptotic and necrotic cells were followed by flow cytometry using an annexin-V-FITC/PI kit. The percentage of cells located in right histogram quadrants is indicated, (a) Cells from ATL acute form, (b) normal, non stimulated PBMC5 (c) non stimulated CIB cell line (B) (a) Annexin-V staining of activated leukocytes from acute ATL patients incubated with 30.9 (closed line), VP 16 (discontinuous line) or A24 (continuous line), (b) Mitochondrial depolarization revealed by DIOC staining of activated leukocytes from ATL acute patient incubated with 30.9 (closed line), VP 16 (discontinuous line) or A24 (b, continuous line). Data represents one out of three different experiments.

Figure 7:
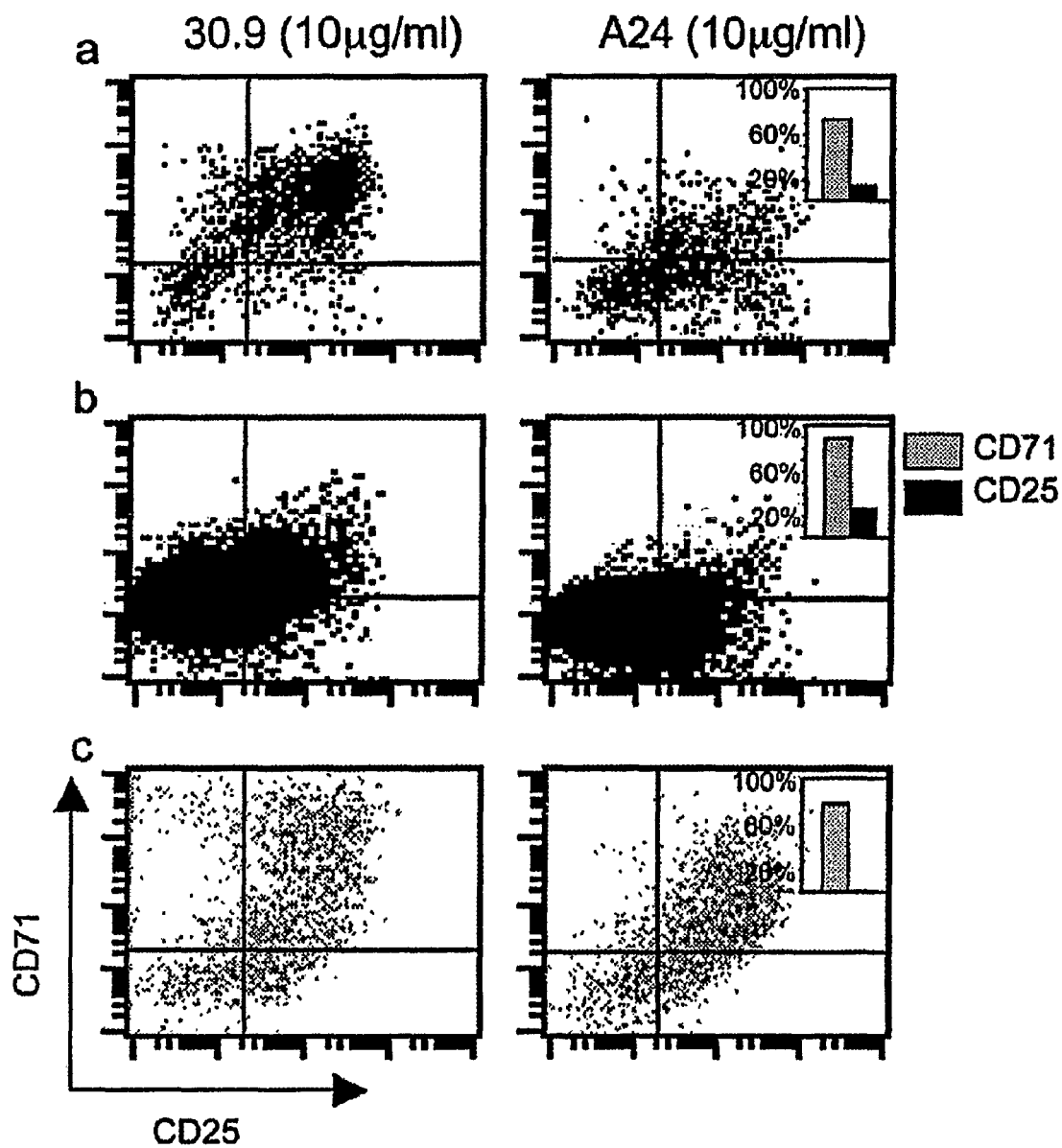
FIGS. 7A,B,C illustrate that A24 can affect TfR expression at the cell surface. The Inhibition percentage of mean fluorescence intensity linked to TfR and CD25 expression is indicated in histograms located in the up-right corner of right panels.

Dead cells were stained by PI, which enters cells that have a disrupted plasma membrane and intercalates to DNA. Following treatment with A24, tumor cells derived from ATL acute patients showed an increase in the number of dead cells (annexin V-PI bright) compared with cells treated with the control antibody. VP 16 at 100 ng/ml was used as an apoptosis positive control (FIG. 7A). In ATL tumor T cells, a large population that stained brightly with annexin-V appeared after treatment with A24 or VP 16. Apoptosis induced by A24 in the TSP-derived cell line CIB (a cell model of non-acute ATL) was also analyzed. A24 induced apoptosis of CIB cell line cultured without PHA-IL2 (FIG. 7A). As a control we included an analysis of normal and untreated PBMC that are not proliferating and that do not undergo spontaneous apoptosis in the absence of activating factors. These cells were not sensitive to A24 (FIG. 7A). DIOC was used, to examine whether mitochondrial depolarization was involved in A24-dependent apoptosis. The drastic reduction in the DIOC concentration that was observed after exposure to A24 or VP 16, showed that apoptosis was induced through the mitochondrial pathway (FIG. 7B).

Example 8

Comparative Activities of A24 and Anti-CD20 on Cell Proliferation in Mantle Cells Lymphoma Mantle cell lymphoma (MCL) is an aggressive non-Hodgkin's lymphoma against which few effective chemotherapies are available. We thus compared the effectiveness of A24 with respect to an anti-CD20 antibody (Rituximab, manufactured by Genentech) lately proposed for the therapeutic of this disease.

Figure 8:
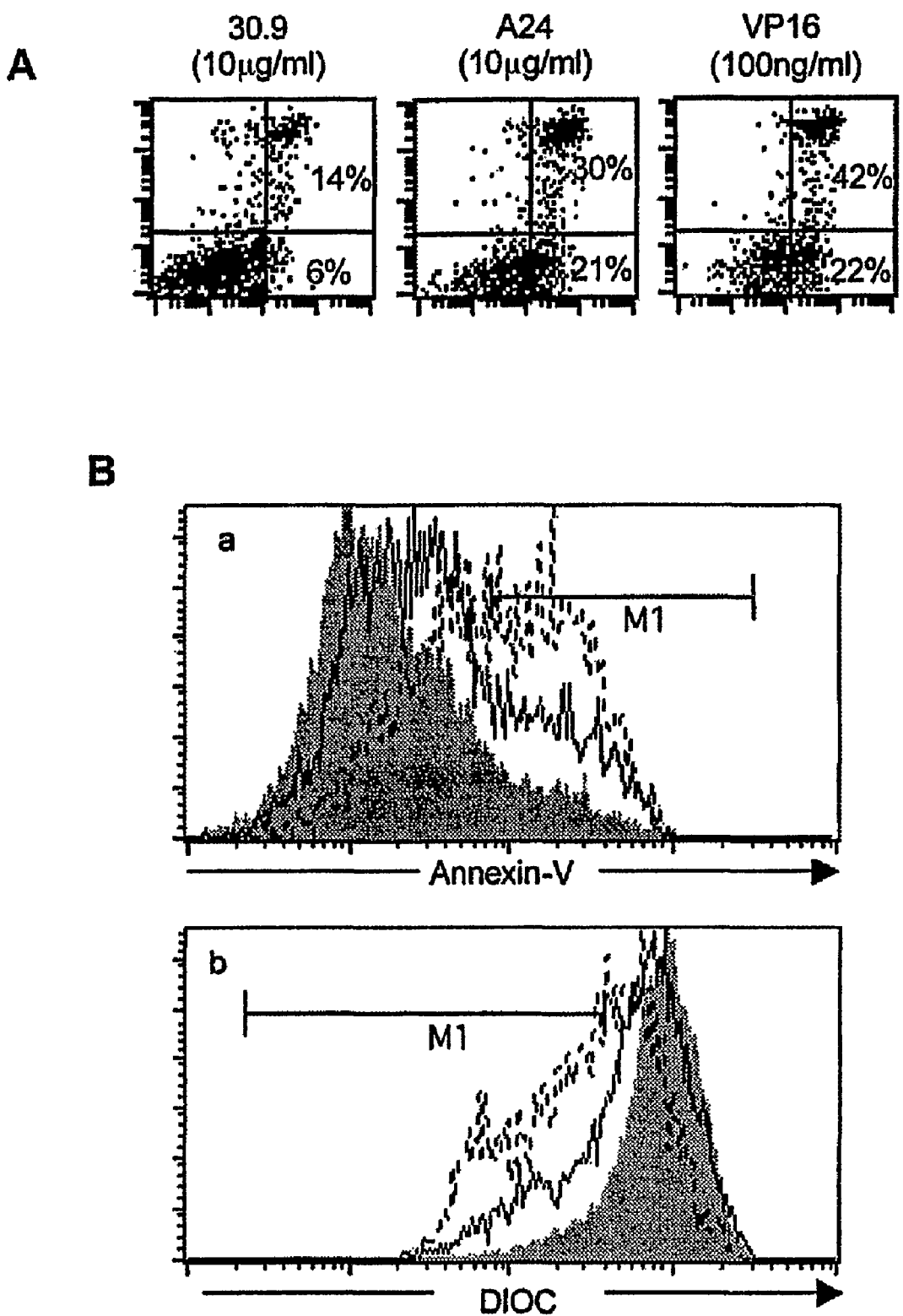
FIGS. 8A,B illustrate the comparative effect of A24, 309.9 and VP16 on the induction of programmed cell death. Cells were activated or not with PHA and IL-2 and incubated in the presence of 30.9, A24 and VP 16. In ATL tumor cells, a large population that stained brightly with annexin-V appeared after treatment with A24 or VP 16. As a control, normal and untreated PBMC were used, which are not sensitive to A24, and, hence DIOC was used to examine whether mitochondrial depolarization was involved in A24-dependent apoptosis.

In a first time, we checked by flow cytometry the rate of expression of TfR and CD20 on five B-cells lines (EBV+ and EBV$^-$) derived from MCL5. using an anti-CD71-PE antibody (Beckman-Coulter) and an anti-CD20-PE antibody (Becton Dickinson). The results are shown on FIGS. 8A and B. The gray histograms respectively represent the rate of expression of the CD71 (A) and of the CD20 (B) at the surface of MCL cells EBV+ (a,b,c,e,f,g) or EBV$^-$ (d). This rate is specified on each histogram after substraction of the background noise of the staining.

Both EBV+ and EBV$^-$ lines express at variable rates the and CD20 and are thus likely to be sensitive to treatments by these two antibodies.

Figure 9:
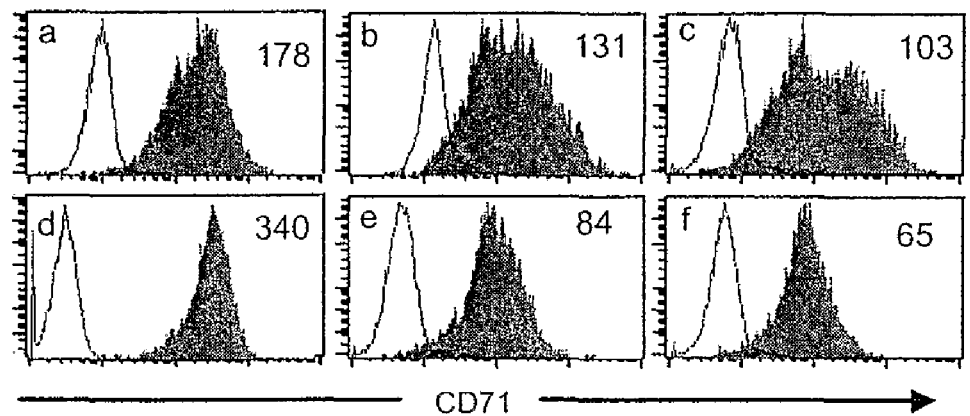
FIGS. 9 A,B illustrate histograms representing, respectively, the rate of expression of the CD71 (A) and the CD20 (B) at the surface of MCL cells EBV+(a,b,c,e,f,g) or EBV-(d).
Figure 9:
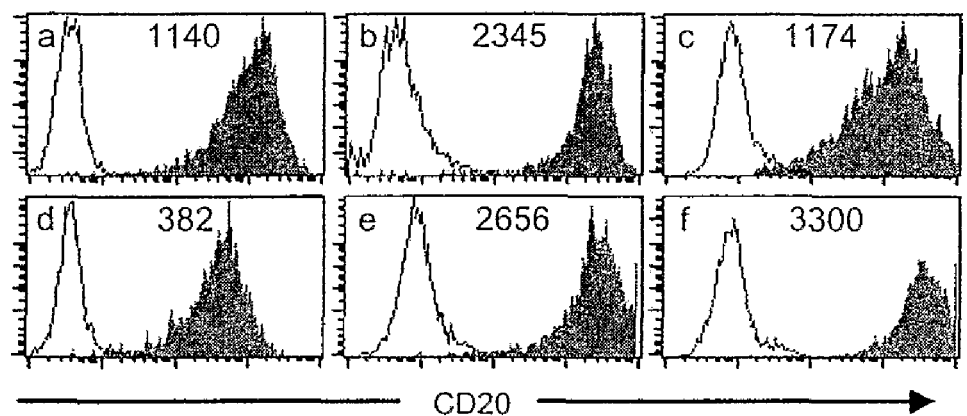

The rate of expression of the target receptors TfR and CD20 at the surface of a MCL cell line EBV+ and a MCL cell line EBV$^-$ after a 30 minutes to 72 hours treatment with A24 (IC$_{50}$=0.625 µg/ml) or Rituximab (10 µg/ml) was followed by flow cytometry as indicated above. The results are shown on FIGS. 9A (A24) and 9B (Rituximab).

Under A24 treatment, the expression of TfR at the surface of the cells decreases by 50% after 30 minutes of treatment and that this reduction reaches more than 80% after 48 hours. On the other hand, the treatment of the cells by Rituximab does not induce notable reduction in the expression of the CD20 whatever the duration of the treatment (30 minutes to 72 hours).

The anti-proliferative effect of A24 and Rituximab on the MCL cells were also compared.

Figure 10:
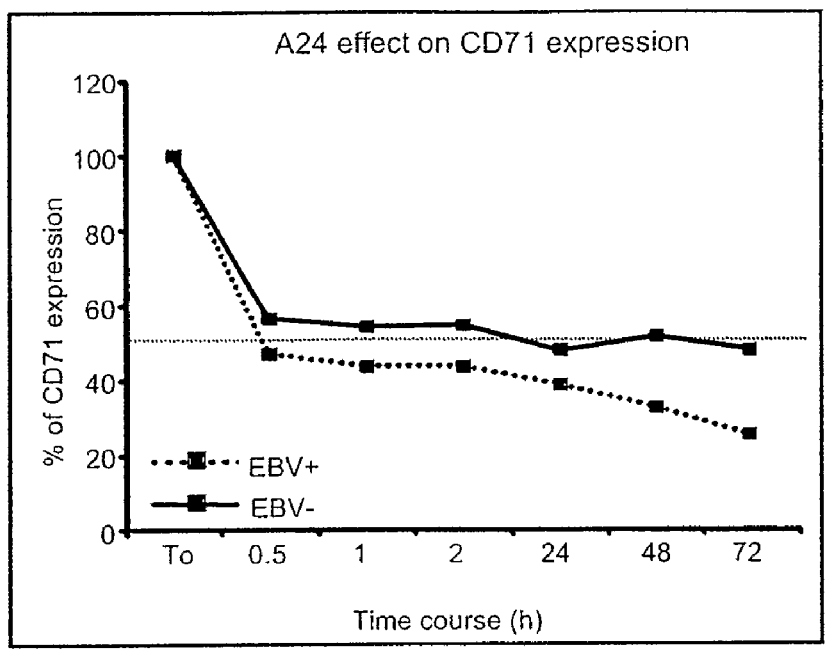
FIGS. 10 A,B illustrate the effect of A24 on CD71 expression, and of Rituximab on CD20 expression, respectively.
Figure 10:
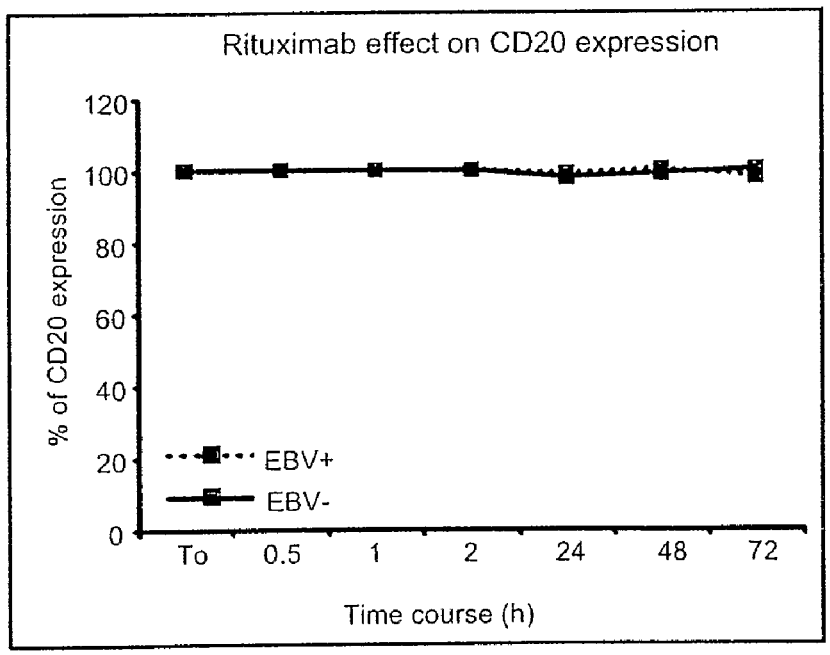
Figure 11:
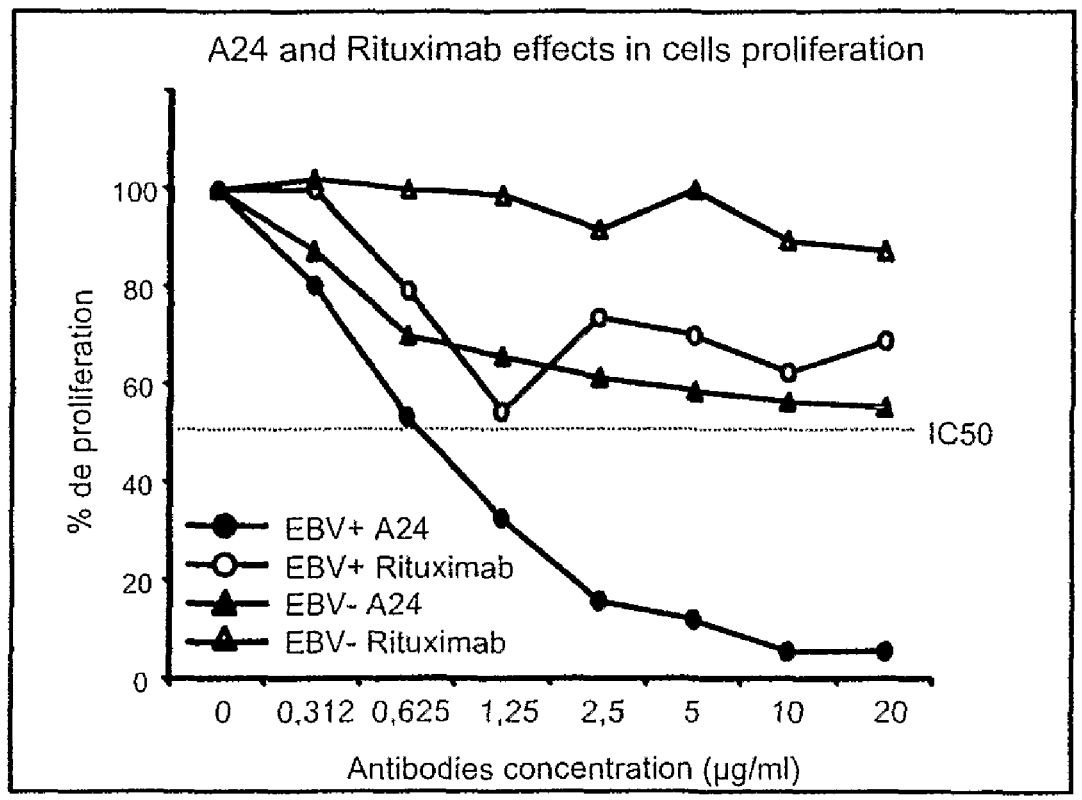
FIG. 11 illustrates the effects of A24 and Rituximab on cell proliferation.

The EBV+ and EBV⁻ MCL lines were cultivated for 72 hours in the presence of concentrations of Rituximab or A24 ranging from 0.312 µg/ml to 20 µg/ml before incorporation of radioactive thymidine (18 h). The cellular proliferation is expressed as a percent of the proliferation of untreated control cells. The results are shown on FIG. 10.

Rituximab as well as A24 are able to reduce the proliferation of the MCL cells but at different rates. Rituximab does not induce more than 20% of inhibition of MCL proliferation, whereas in same time A24 inhibits it from 40 to 80%. This difference is mainly due to the requirement of ADCC for a good effectiveness of Rituximab contrary to A24. Moreover, the anti-proliferative effect of A24 is obtained with a very low $IC_{50}$ (0.625 µg/ml).

Example 9

Effect of A24 Antibody on Polymeric IgAI (pIgAI) Induced Mesangial Cell Proliferation Mesangial cell proliferation is a characteristic of IgA nephropathy, the first cause of renal failure worldwide. There is currently no efficient treatment available, and the disease aggravates towards renal failure.

It has been shown that IgA can induce mesangial cell proliferation (GOMEZ-GUERRERO et al. J Immunol 151: 5247, 1994); it is also known that TfR is overexpressed by mesangial cells of patients with IgA nephropathy (MOURA et al, 2001, cited above; HADDAD et al J Am Soc Nephrol. 2003, 14: 327-337).

The inventors have tested whether the blocking of TfR by A24 could inhibit pIgA1-induced mesangial cell proliferation.

Cultures of mesangial cells were obtained as described by MOURA et al, (2001, cited above). These cultures were incubated for 24 hours with RPMI medium+foetal calf serum (control), or with polymeric IgAI (pIgA1) alone at 500 µg/ml, or with pIgA1 (10 µg/ml) in combination with A24 at 10 µg/ml or with the control antibody 30.9 at the same concentration.

FIG. 12A shows that pIgA1 induced a 70% increase in mesangial cells proliferation. A24 specifically blocked this IgA-induced mesangial cell proliferation whereas the 30.9 isotype control did not.

It was also determined whether the effect of A24 on pIgA1-mediated mesangial cells proliferation was the result of inhibition of pIgA1-mediated functions, or the result of an interference with iron metabolism depriving the cells of their iron uptake.

Figure 12:
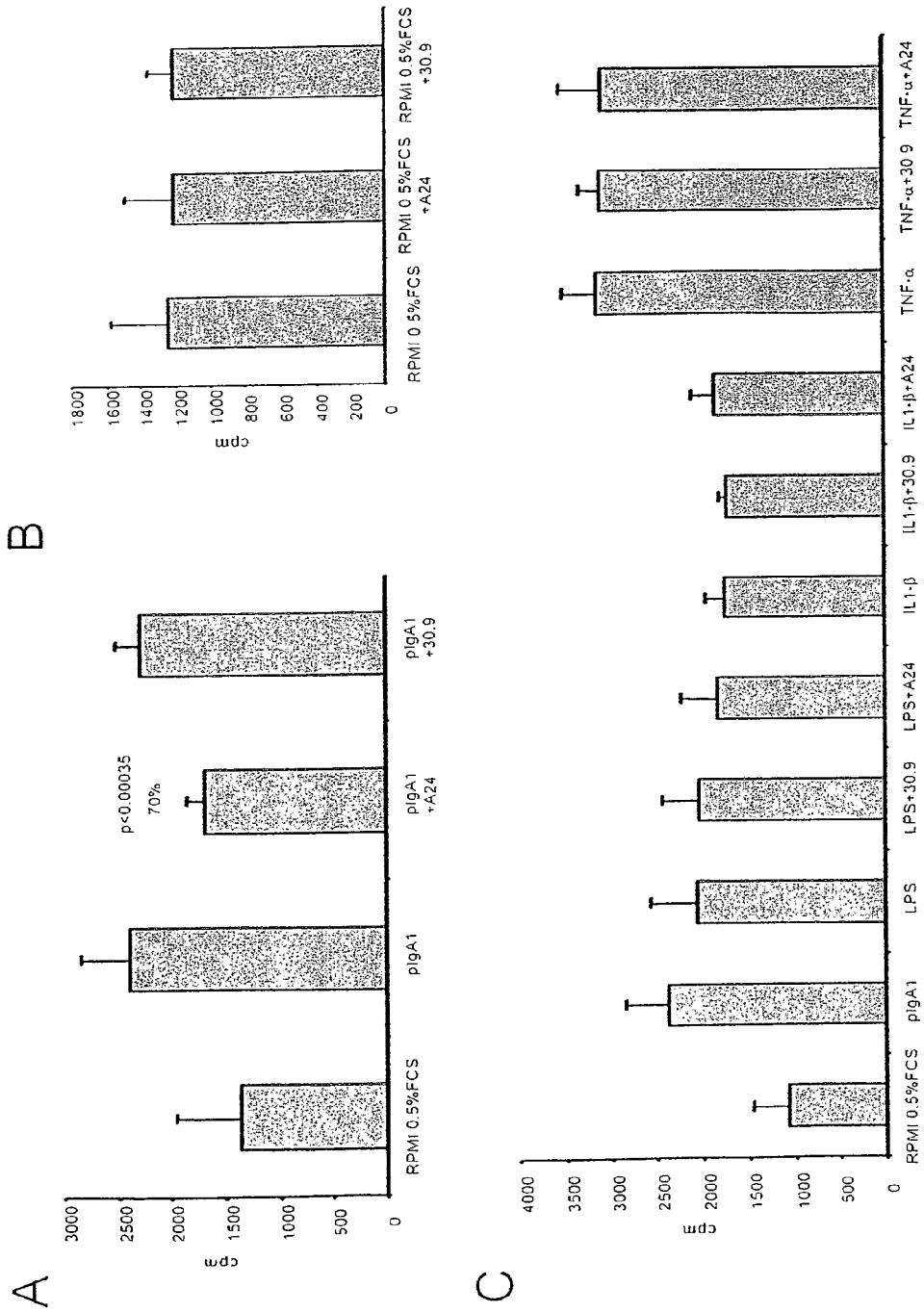
FIGS. 12 A,B,C illustrate the following: A) that plgA1 induced a 70% increase in mesangial cell proliferation, and A24 specifically blocked this IgA-induced mesangial cell proliferation whereas the 30.9 isotype control did not; B) that A24 alone (10 µg/ml) had no effect on the low proliferative mesangial cells; and C) that A24 had no significant effect on mesangial cell proliferation induced by cytokines or LPS.

FIG. 12 B shows that A24 alone (10 µg/ml) had no effect on the low proliferative mesangial cells.

To test whether A24 inhibited mesangial cells proliferation induced by other stimuli than pIgA1, we performed experiments with LPS (10 µg/ml) and pro-inflammatory cytokines that are known to induce mesangial cell proliferation: IL1-13 (10 ng/ml) and TNF-α (10 ng/ml).

FIG. 12 C shows that A24 had no significant effect on mesangial cells proliferation induced by cytokines or LPS.

Therefore, the anti-TfR mAb A24 specifically blocks pIgA1-induced mesangial cells proliferation.

In addition experiments, we have shown that A24 blocks IgA-mediated induction of TfR expression on the surface of mesangial cells (data not shown).

The invention claimed is:

1. An isolated antibody which binds specifically to the transferrin receptor (TfR) and blocks binding of transferrin to the receptor, wherein the antibody is antibody A24 produced by the hybridoma cell line CNCM 1-2665.

2. An isolated antibody, which binds specifically to (TfR) and blocks binding of transferrin to the (TfR), wherein the antibody is a recombinant antibody comprising CDR1, CDR2 and CDR3 of light and heavy chains of A24.

3. The antibody of claim 2, which is selected from the group consisting of a chimeric antibody and a humanized antibody.

4. A fragment of an antibody of claim 1, which is selected from the group consisting of Fv, Fab, Fab'2 or scFv fragments thereof.

5. A fragment of an antibody of claim 3, which is selected from the group consisting of Fv, Fab, Fab'2 or scFv fragments thereof.

6. A recombinant protein comprising the antibody of claim 1, fused to a heterologous polypeptide.

7. A recombinant protein comprising the Fv, Fab, Fab'2 or scFv fragments of claim 4, fused to a heterologous polypeptide.

8. The antibody of claim 1, which blocks binding of transferrin to the (TfR) competitively.

9. The antibody of claim 1, which reduces TfR expression and impairs TfR recycling in TfR-expressing tumor cells.

10. The antibody of claim 1, which induces apoptosis of target ATL tumor cells.

11. The antibody of claim 9, wherein the TfR-expressing tumor cells are ATL tumor cells.

* * * * *